(12) United States Patent
Sheppard et al.

(10) Patent No.: US 8,740,922 B2
(45) Date of Patent: Jun. 3, 2014

(54) EAR PIPE (75) Inventors: Russell Lee Sheppard, Newcastle, CA (US); Troy Healy, Auburn, CA (US)

(73) Assignee: Wally's Natural Products, Auburn, CA (US)

( * ) Notice: Subject to any disclaimer, the term of this patent is extended or adjusted under 35 U.S.C. 154(b) by 0 days.

(21) Appl. No.: 13/159,214

(22) Filed: Jun. 13, 2011

(65) Prior Publication Data
US 2012/0316587 A1 Dec. 13, 2012

(51) Int. Cl.
*A61F 11/00* (2006.01)
(52) U.S. Cl.
USPC .......................................... 606/162
(58) Field of Classification Search
USPC ............ 606/162, 109; 600/562; 131/180, 196
See application file for complete search history.

(56) References Cited

U.S. PATENT DOCUMENTS

| 3,524,453 | A | * | 8/1970 | Halaby | 131/174 |
|---|---|---|---|---|---|
| 3,651,808 | A | * | 3/1972 | White | 604/213 |
| 4,203,456 | A | * | 5/1980 | Miller | 131/230 |
| 4,870,979 | A | * | 10/1989 | Browning et al. | 131/196 |
| 6,059,803 | A | * | 5/2000 | Spilman | 606/162 |
| 6,155,987 | A | * | 12/2000 | Scherl | 600/562 |
| 6,432,117 | B1 | * | 8/2002 | Murray | 606/162 |
| 7,273,467 | B1 | * | 9/2007 | Mezzoli | 604/43 |
| 7,624,734 | B2 | * | 12/2009 | Balch et al. | 128/203.27 |
| 2002/0004664 | A1 | * | 1/2002 | Gerstein | 606/162 |
| 2005/0096678 | A1 | * | 5/2005 | Olson | 606/162 |
| 2007/0167918 | A1 | * | 7/2007 | Reed et al. | 604/187 |
| 2011/0071560 | A1 | | 3/2011 | Sheppard | |

FOREIGN PATENT DOCUMENTS

EP 0908161 A1 4/1999

* cited by examiner

*Primary Examiner* — Thomas McEvoy
*Assistant Examiner* — Julie A Szpira
(74) *Attorney, Agent, or Firm* — Amin Talati, LLC; Yuri Astvatsaturov; George M. Carrera, Jr.

(57) ABSTRACT

An ear pipe used as an alternative medicine practice to remove excess ear wax, debris, and other undesirable contaminants from the ear canal. The ear pipe includes a generally hollow body, wherein the hollow body includes a bowl, a midsection, and a proximal end. The ear pipe may be used by bringing a unit of ear pipe fuel to a smoldering state within the bowl, holding the ear pipe with a user's hand, and inserting the proximal end of the pipe into a user's ear to allow warm air/smoke to enter the ear canal and create temperatures high enough to cause the excess ear wax, debris, and other undesirable contaminants to drain from the ear canal.

22 Claims, 11 Drawing Sheets

EAR PIPE

BACKGROUND

Ear candling, also known as thermal-auricular therapy or ear coning, is an alternative medicine practice that has been used for thousands of years to remove excess ear wax, debris, and other undesirable contaminants from the ear canal. It is believed that this practice may date back to the ancient cultures of pre-Columbian Native Americans, Tibetans, Chinese, and Egyptians.

Use of ear candles to remove excess ear wax and other debris from the ear canal may help to maintain and/or improve the quality of a person's hearing. Over time, the effects of allergies and sicknesses (colds, flu, sinus problems, etc.) can cause a buildup of wax and other debris in the ear canal. Also, extensive use of various appliances, including telephones and hearing appliances (hearing aids), can induce build up of wax in the ear canal. Eventually, the buildup of wax and other debris can be so great as to cause a natural "ear plug" that can alter a person's hearing capabilities. In many instances, an effective cleaning of the ear canal using ear candles can lead to a larger range of hearing frequency. Ear candles are also used to enhance drainage of toxins exiting the body through the ear canal. For instance, the Eustachian tube connects the middle ear with the nose and throat. When the Eustachian tube becomes clogged with excessive ear wax, an infection may develop. Infection can also occur when one of the body's systems is trying to purge toxins, in liquid form, through the ear canal.

When using conventional ear candles, the top end of the ear candle is lit, and as it burns, smoke begins to billow out of the bottom of the cone-shaped ear candle. The bottom end is then placed snugly into the ear canal to form an air tight seal between the open bottom end of the ear candle and the ear canal. As the ear candle continues to burn, air is forced back up through the hollow, cone-shaped ear candle, creating a warm air current through the ear candle towards the top burning end. This results in a warm vacuum, creating suction at the bottom end of the ear candle and within the ear canal. The warm air melts the ear wax and the created suction pulls the wax and other debris from within the ear canal and through the bottom end of the ear candle. The liquid wax hits the sides of the cooler candle, solidifying on the inside surface of the candle. As the ear candle continues to burn, some of the ear wax may burn off while the remainder collects within the hollow candle, particularly near the bottom end.

Ear candling may prove (or is generally believed) to be more effective than other conventional methods of cleaning the ears. For instance, repeated water cleansings can create a prolonged moist environment that can invite growth of bacteria and fungus which may lead to an infection of the middle and/or inner ear. Also, because wax is a natural repellant of water, cleaning the ear canal with water is not entirely effective in removing ear wax and other debris. Moreover, water can become trapped in the ears after cleansing, causing an annoying noise and minor discomfort. Other physical removal methods, such as swabbing with a cotton swab, may also not be effective.

While ear candling is an effective method for cleaning the ear canal, there are some drawbacks to using conventional ear candles. For example, as the ear candle burns down and becomes shorter, the flame on the end of the candle burns close to the ear and hair of the user. This creates a concern for both the comfort and safety of the user. For this reason, users of ear candles may extinguish them early, leaving a significant portion of the ear candle unused. This in turn requires use of a greater number of ear candles to accomplish a complete ear cleaning. Additionally, improper usage of conventional ear candles has been known to result in injuries caused by the flame or the smoldering tip of the candle.

For the foregoing reasons, there is a need for a device that provides greater ease of use, convenience, safety, and efficiency.

SUMMARY

The present invention is directed to an apparatus that satisfies the need for a safer and more efficient apparatus that can be used in place of a conventional candle for ear candling. In one embodiment, the presently claimed invention comprises a generally hollow body, wherein the generally hollow body includes a bowl disposed at a distal end of the pipe, a midsection, and a proximal end, wherein the midsection extends upward from at least a portion of an upper surface of the bowl to the proximal end of the generally hollow body, wherein the proximal end is open.

In another embodiment, the presently claimed invention comprises a generally hollow body, wherein the generally hollow body includes a bowl disposed at a distal end of the pipe, a midsection, and a proximal end, wherein the midsection extends upward from at least a portion of an upper surface of the bowl to the proximal end of the generally hollow body, wherein the proximal end is open, and an ear tip positioned adjacent to the proximal end of the generally hollow body, wherein the ear tip includes an axially aligned pass-through opening, an ear contact portion, and an ear contact end.

In yet another embodiment, the presently claimed invention may be part of a kit wherein the kit comprises a pipe, the pipe comprising a generally hollow body with an external and an internal surface, wherein the generally hollow body includes, a bowl disposed at a distal end of the pipe, a midsection extended upward from at least a portion of an upper surface of the bowl to a proximal end of the generally hollow body wherein the proximal end is open, a fuel cover arching over the upper surface of the bowl and covering the bowl, and at least one support member positioned within and supported by the bowl, at least one ear tip, wherein the tip is positioned adjacent to the proximal end of the generally hollow body, and at least one unit of ear pipe fuel.

BRIEF DESCRIPTION OF THE DRAWINGS

These and other features, aspects, and advantages of the presently claimed invention will become better understood with regard to the following description, appended claims, and accompanying drawings where:

DESCRIPTION

The following description and examples further illustrate the invention but, of course, should not be construed as in any way limiting its scope.

| Pipe | 10 |
| Generally hollow body | 15 |
| Bowl | 20 |
| Distal end | 25 |
| Midsection | 30 |
| Open proximal end | 35 |
| Body side portion A | 40A |
| Body side portion B | 40B |
| Body top portion (no integrated fuel cover) | 41A |
| Body bottom portion | 41B |
| Body top portion (integrated fuel cover) | 42A |
| Body bottom portion | 42B |
| Fastening post(s) on side portion 40A | 45A |
| Receiving opening(s) on side portion 40B | 45B |
| Fastening post(s) on bottom portion 41B | 46A |
| Receiving opening(s) on top portion 41A | 46B |
| Fastening post(s) on bottom portion 42B | 47A |
| Receiving opening(s) on top portion 42A | 47B |
| Fuel cover | 50 |
| Fuel cover fastening post(s) | 55A |
| Fuel cover receiving opening(s) | 55B |
| Alignment hook receiving notch | 60 |
| Alignment hook | 65 |
| Vent holes (ventilation openings) | 70 |
| Support leg(s) | 72 |
| Support member (mesh) | 75 |
| Support ledge | 77 |
| Ear pipe fuel | 80 |
| Elongated outward-facing opening | 85 |
| Support member indentation | 90 |
| Ear tip | 95 |
| Ear tip opening | 100 |
| Ear contact portion | 105 |
| Ear contact end | 110 |
| Transitional region | 115 |
| Ear tip stem | 120 |
| Stem base | 125 |
| Stem end | 130 |
| Ear tip skirt/flange | 135 |
| Curve | C |
| User | 200 |
| User's ear | 210 |
| Ear canal | 220 |

Figure 1:
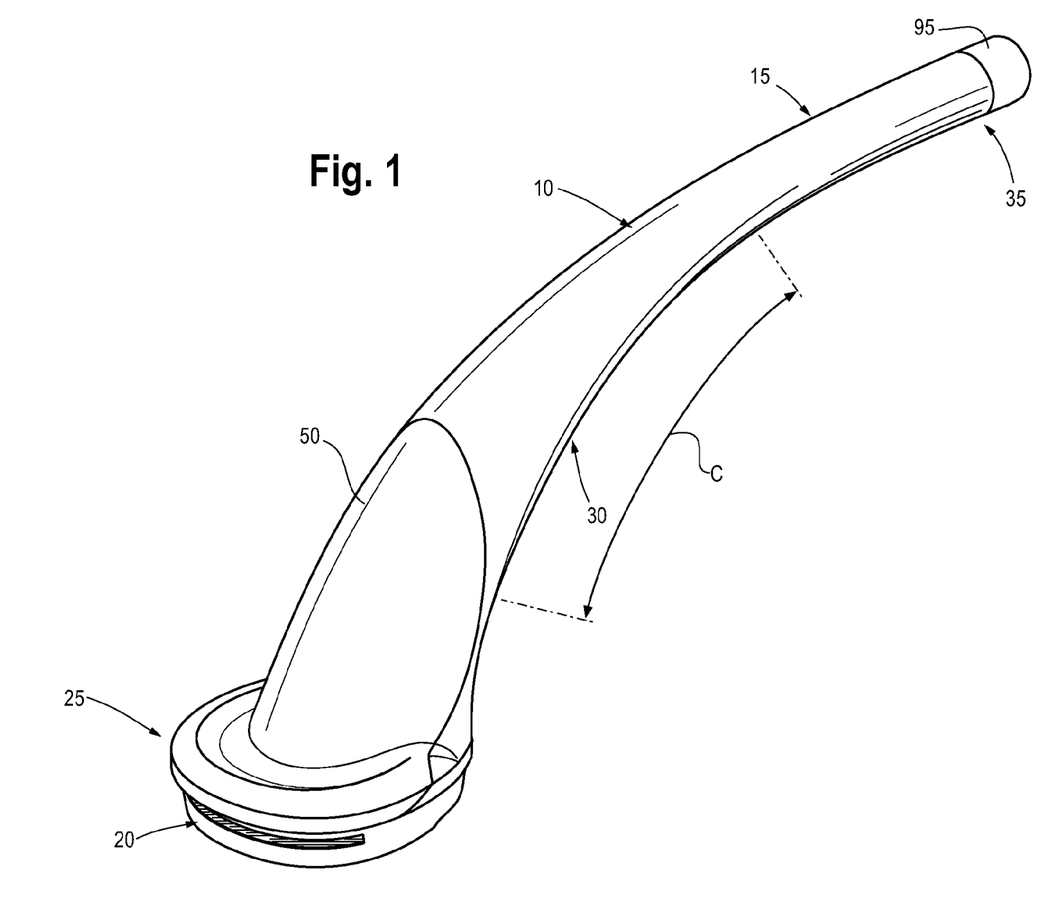
FIG. 1 shows a perspective view of an embodiment of the presently claimed invention.

Referring to the drawings, the ear pipe is shown and generally indicated as device 10. Referring to FIG. 1, Pipe 10 is generally defined by a generally hollow body 15 having a generally curved shape ("C") with internal and external surfaces, the generally hollow body 15 having a bowl 20 disposed at a distal end 25, and a midsection 30. The midsection 30 extends upwards from at least a portion of an upper surface of the bowl 20 to an open proximal end 35 of the generally hollow body 15. The angle and the shape of the curve C of the generally hollow body 15 may be adjusted as needed for various embodiments with the shape of the curve C ranging from a smooth bend to a sharp elbow (i.e. angular).

Preferably, the generally hollow body 15 is curved and the radius and shape of said curve C are optimized to provide a path of least resistance for any gas moving from the distal end 25 to the proximal end 35. The pipe's midsection 30 may further include a flexible section which may allow the user to adjust the curvature and/or angle between the proximal and the distal ends (25, 35).

The generally hollow body 15 may be made from any commercially available material that can sustain an elevated temperature without substantial degradation and/or combustion. Preferably, such material possesses superior insulation and low heat transfer properties so as to allow a user to handle the device without the risk of injury such as a burn. In one embodiment, the material used for construction of the generally hollow body 15 may be selected from materials including, but not limited to, wood, plastic, polycarbonate, metal, stone, clay, glass, ceramic, rubber, or the like, and any combination thereof.

In an embodiment, the generally hollow body 15 has an overall tapered shape from the distal end 25 to the proximal end 35, wherein the outer diameter of the distal end is greater than the outer diameter of the proximal end. In another embodiment, there is a substantially constant decrease of the outer diameter from the distal end 25 to the proximal end 35. For example, in an embodiment, the outer diameter of the distal end 25 ranges from about 100 millimeters (mm) to about 40 mm, and the outer diameter of the proximal end 35 ranges from about 15 mm to about 8 mm.

Figure 2:
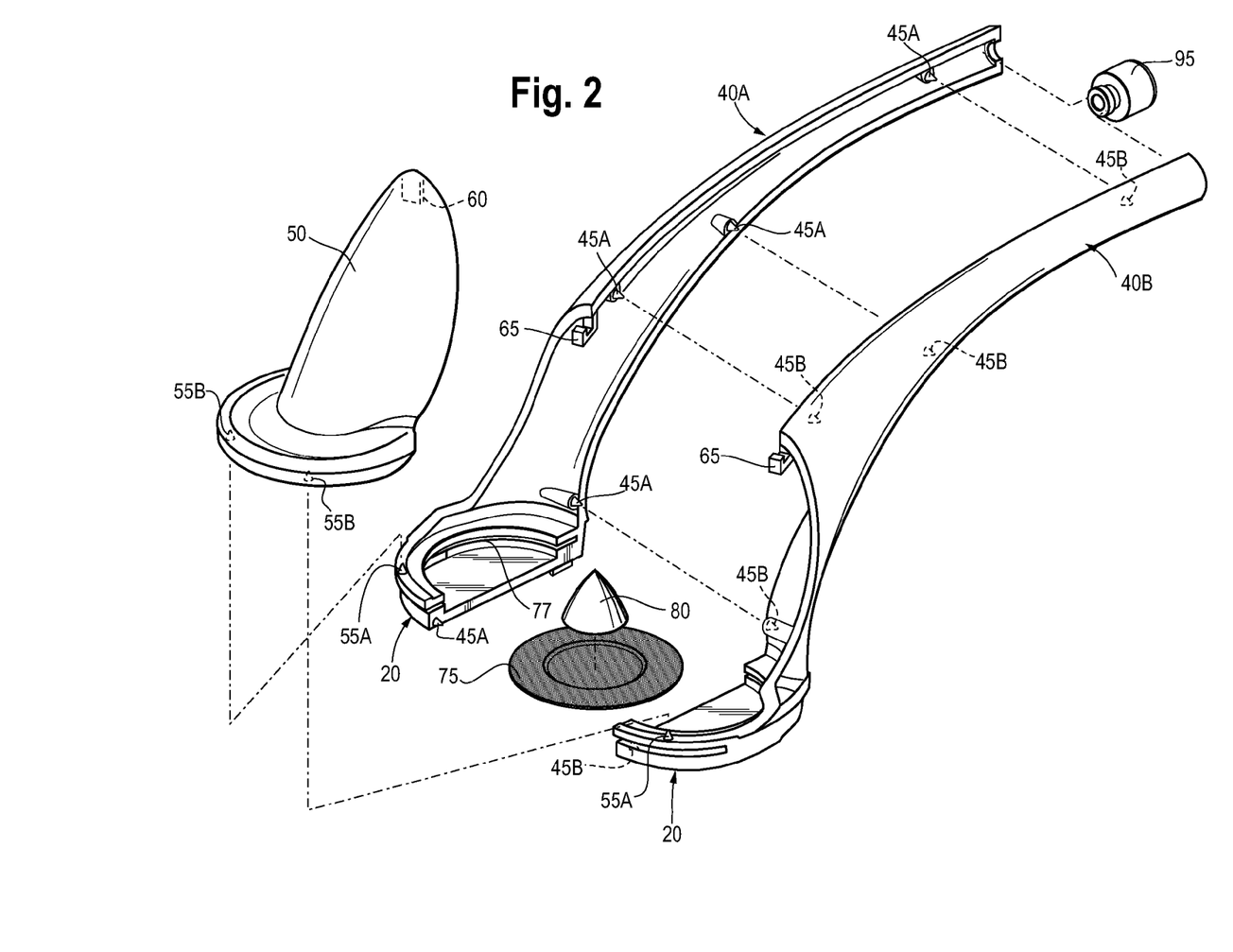
FIG. 2 shows an exploded view of an embodiment of the presently claimed invention.
Figure 3:
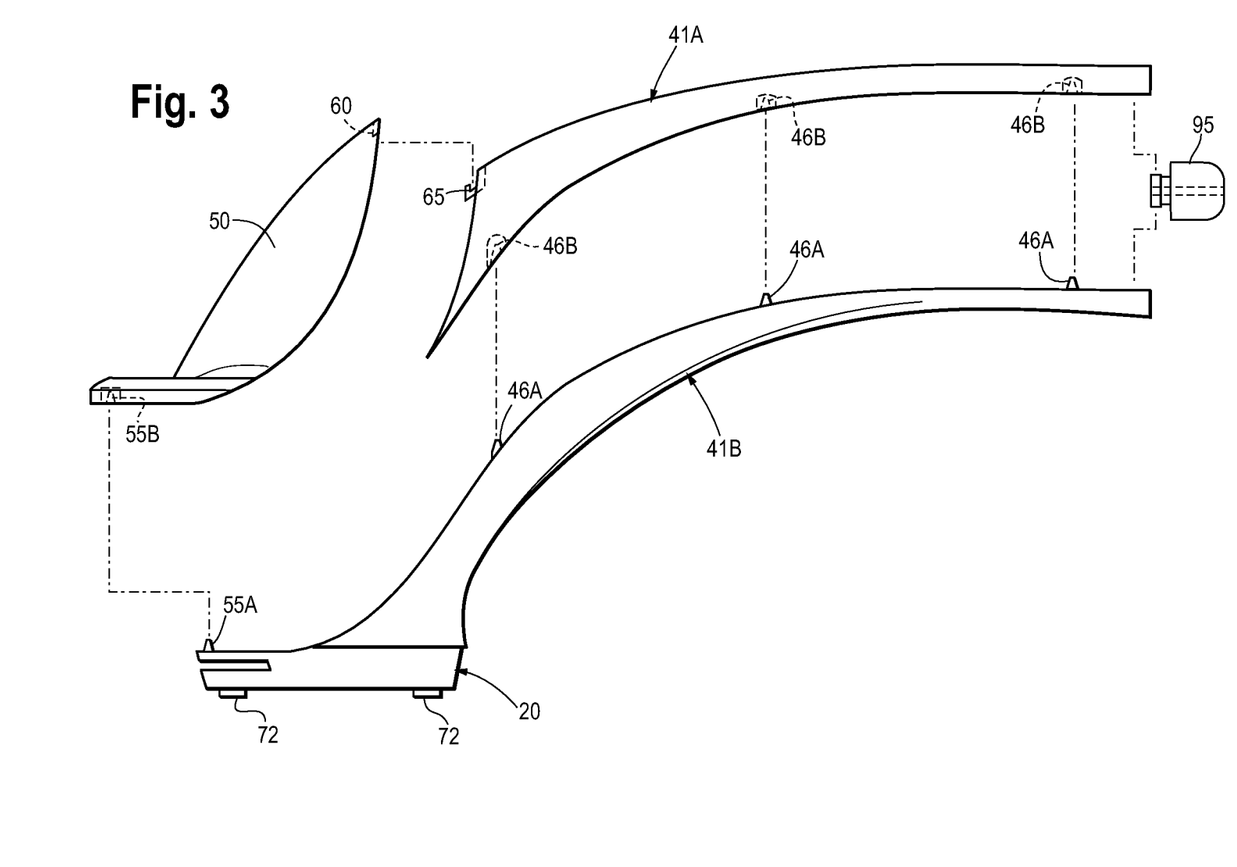
FIG. 3 shows a side view of the presently claimed invention in an embodiment where the presently claimed invention is separable along the transverse plane.

Referring to FIGS. 2 and 3, in a separate embodiment, the generally hollow body 15 may be dismantled into two or more portions to allow the user to remove any debris and clean the internal surface of the pipe 10. The generally hollow body 15 may be separated along at least a portion of a sagittal and/or a transverse plane into two separate portions 40A and 40B (or, alternatively, 41A and 41B) to reveal the internal surface of the pipe. The two portions 40A and 40B (or, alternatively, 41A and 41B) may be fastened together using any conventional means that can join them together to prevent said portions from coming apart unintentionally. In one embodiment, the fastening means are achieved by implementing fastening clips and/or fastening snaps where the fastening clips and/or fastening snaps include a fastening post(s) 45A disposed on or in the first portion 40A of the generally hollow body 15 and a corresponding receiving opening(s) 45B disposed on or in the second portion 40B of the generally hollow body 15 (or, alternatively, fastening post(s) 46A disposed on or in the bottom portion 41B of the generally hollow body 15 and a corresponding receiving opening(s) 46B disposed on or in the top portion 41A of the generally hollow body 15). When both portions 40A and 40B (or, alternatively, 41A and 41B) are joined together, each fastening post 45A (or, alternatively, 46A) enters a corresponding receiving opening 45B (or, alternatively, 46B), thereby providing a locking mechanism that prevents both portions 40A and 40B (or, alternatively, 41A and 41B) from separating without the application of some force or disassembly. In other embodiments, the fastening means may be accomplished by using split pin(s), buckle(s), clamp(s), clasp(s), nut(s) and bolt(s), screw(s), clip(s), clutch(s), flange(s), band(s) of elastic or non elastic material(s), strap(s), hook-and-loop strip(s), magnet(s), or a combination thereof. In another embodiment, the fastening posts 45A (or, alternatively, 46A) can be affixed using glue, cement, adhesive, solder, and the like. In this manner, the portions 40A and 40B (or, alternatively, 41A and 41B) can be firmly affixed or joined, either temporarily or permanently as needed.

Figure 4:
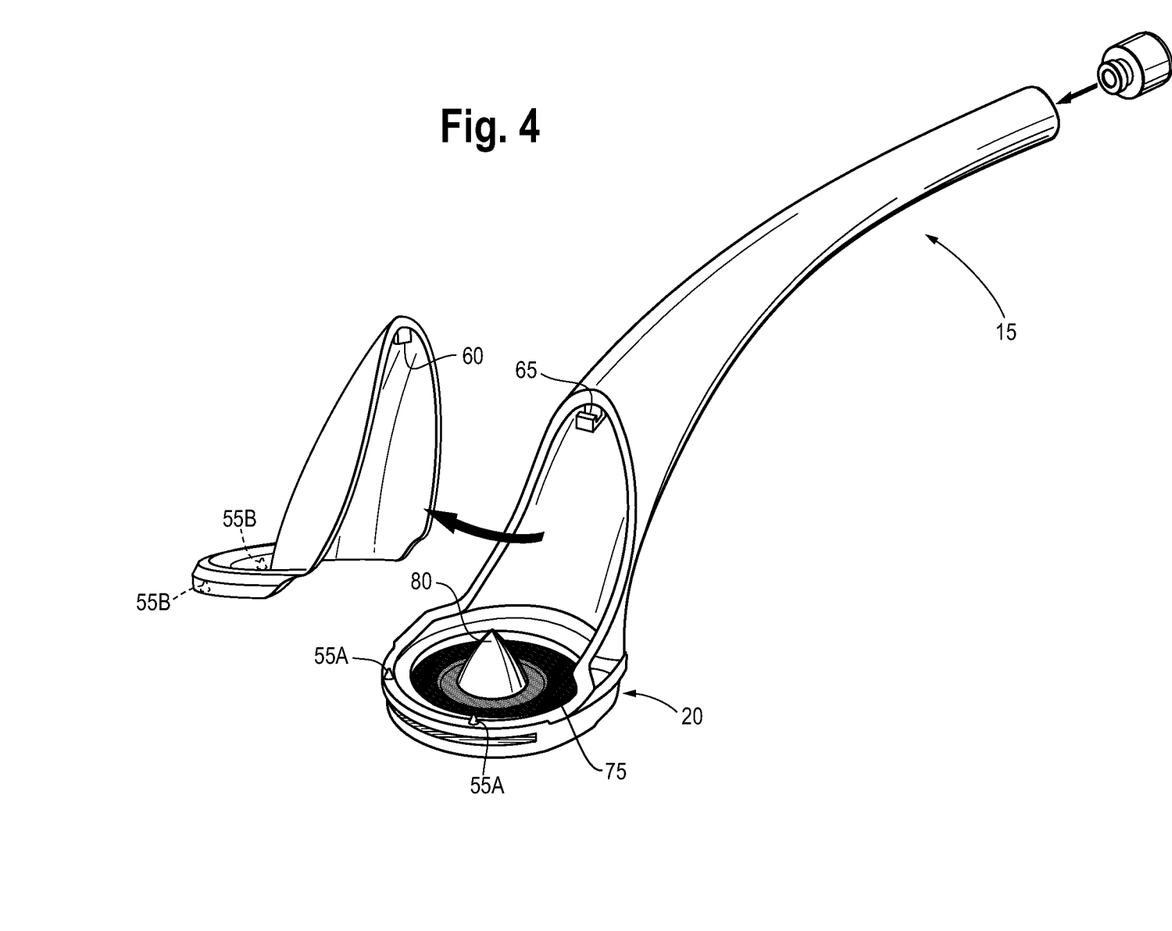
FIG. 4 shows a perspective view of an embodiment of the presently claimed invention showing an alignment hook and a corresponding notch in a fuel cover.

The ear pipe may further comprise an optionally removable fuel cover 50 disposed adjacent to at least a part of the upper surface of the bowl 20. Preferably the fuel cover may follow the overall shape, together with the internal and external surfaces, of the generally hollow body 15. Similar to the generally hollow body 15, the fuel cover 50 may be made from any commercially available material that can sustain an elevated temperature or a direct flame without substantial degradation and/or combustion. Preferably, such material possesses superior insulation and low heat transfer properties to allow a user to handle the pipe and cover without the risk of injury such as a burn. In one embodiment, the material used for construction of the fuel cover 50 may be selected from wood, plastic, polycarbonate, metal, stone, clay, glass, ceramic, rubber, or the like, and any combination thereof. The fuel cover 50 may be removable and/or may be joined or affixed to the generally hollow body 15 using any conventional means that can prevent unintentional separation. In one embodiment, the fuel cover may be placed onto guide post(s) that are disposed on or in the generally hollow body, allowing the fuel cover to rest on said post(s) under its own weight when said post(s) enter corresponding opening(s) disposed on or in the fuel cover. In another embodiment, the fastening means are achieved by implementing fastening clip(s) and/or fastening snap(s) where the fastening clip(s) and/or fastening snap(s) include a fastening post(s) 55A is disposed on or in the generally hollow body 15 and a corresponding receiving opening(s) 55B is disposed on or in the fuel cover 50. Said posts and openings configured and spread in such manner that a precise mating of complementary parts is achieved. For example, a removable fuel cover 50 having receiving openings 55B, could be affixed to fastening posts 55A in lower portion 41B, as shown in FIG. 3. When the optionally removable fuel cover 50 is joined to the generally hollow body 15, each fastening post 55A enters a corresponding receiving opening 55B, thereby providing a securing mechanism that prevents the fuel cover 50 and the generally hollow body 15 from separating without application of some force or disassembly. In yet other embodiments the fastening means may be accomplished by using split pin(s), buckle(s), clamp(s), clasp(s), nut(s) and bolt(s), clip(s), clutch(s), nut(s) and bolt(s), screw(s), flange(s), band(s) of elastic or non elastic material, strap(s), hook-and-loop strip(s), magnet(s), and a combination thereof. Referring to FIG. 4, optionally, an alignment hook 65 is placed in or on the generally hollow body 15 with a corresponding receiving notch 60 cut into the fuel cover 50, for example, on its interior surface.

Figure 5:
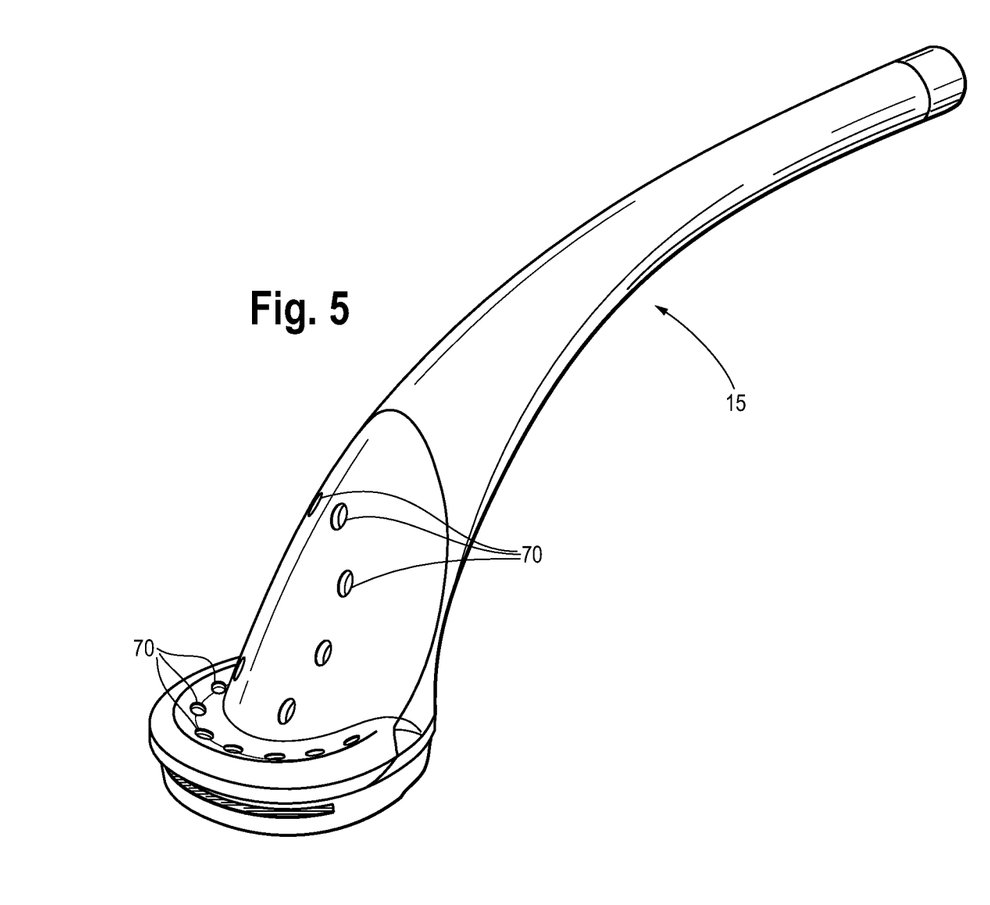
FIG. 5 shows a perspective view of an embodiment of the presently claimed invention showing ventilation holes in the fuel cover.

Referring to FIG. 5, the fuel cover may optionally include a ventilation opening(s) 70 (or vent holes) which may provides a pathway for air to be drawn into the pipe and aid in the smoldering of ear pipe fuel. In one embodiment, the ventilation opening(s) 70 have a diameter ranging from about 1 mm to about 6 mm. There may be a multiplicity of ventilation openings 70, configured and spread in such manner that adequate ventilation and/or movement of air is achieved.

Figure 6:
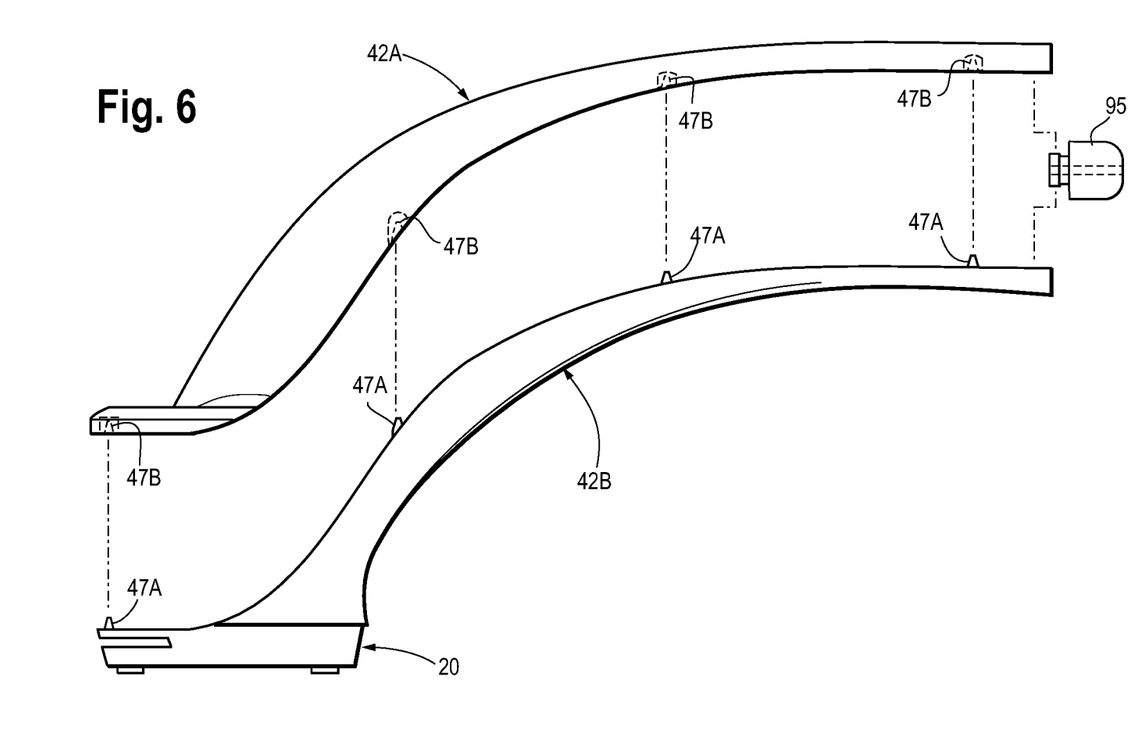
FIG. 6 shows a side view of the presently claimed invention in an embodiment where the presently claimed invention is separable along the transverse plane and the fuel cover is integrated into a top portion.

While the removability of the fuel cover 50 may be desired by the need to place ear pipe fuel inside the pipe, depending on the embodiment of the presently claimed invention, the fuel cover 50 is optional. For example, in one embodiment of the presently claimed invention which allows for the separation of the generally hollow body 15 along the transverse plane (as described above and shown in FIG. 6) the complete top portion 42A of the ear pipe 10 may be removed. In such embodiment, the fuel cover is an integral part of the top portion 42A of the generally hollow body 15. Thus, top portion 42A is connected, joined, or affixed to lower portion 42B as described above in previous embodiments using fastening post(s) 47A and corresponding receiving opening(s) 47B.

Figure 7:
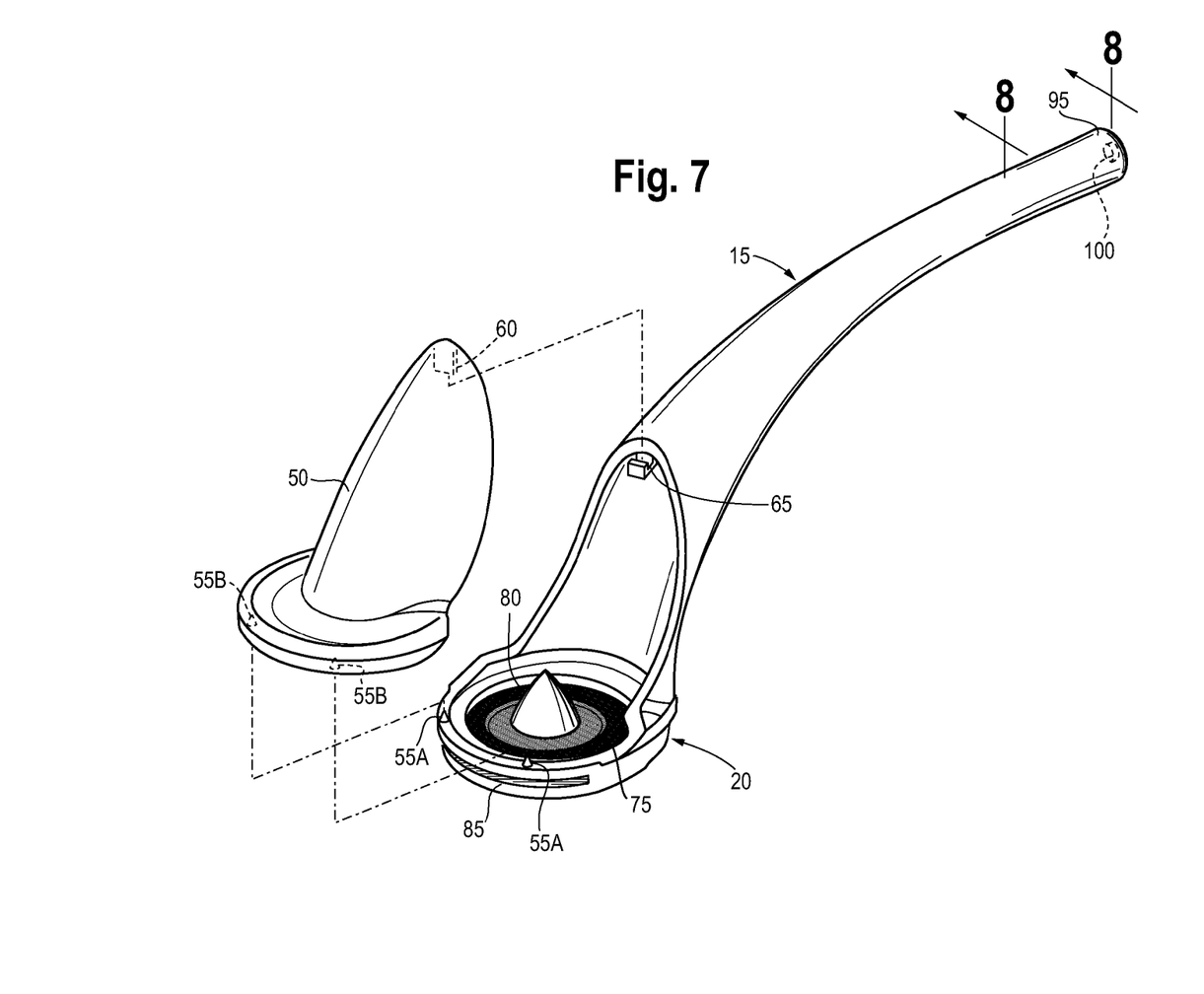
FIG. 7 shows a perspective view of the presently claimed invention in an embodiment where an ear tip is an integral portion a generally hollow body.
Figures 11, 11B, 11C:
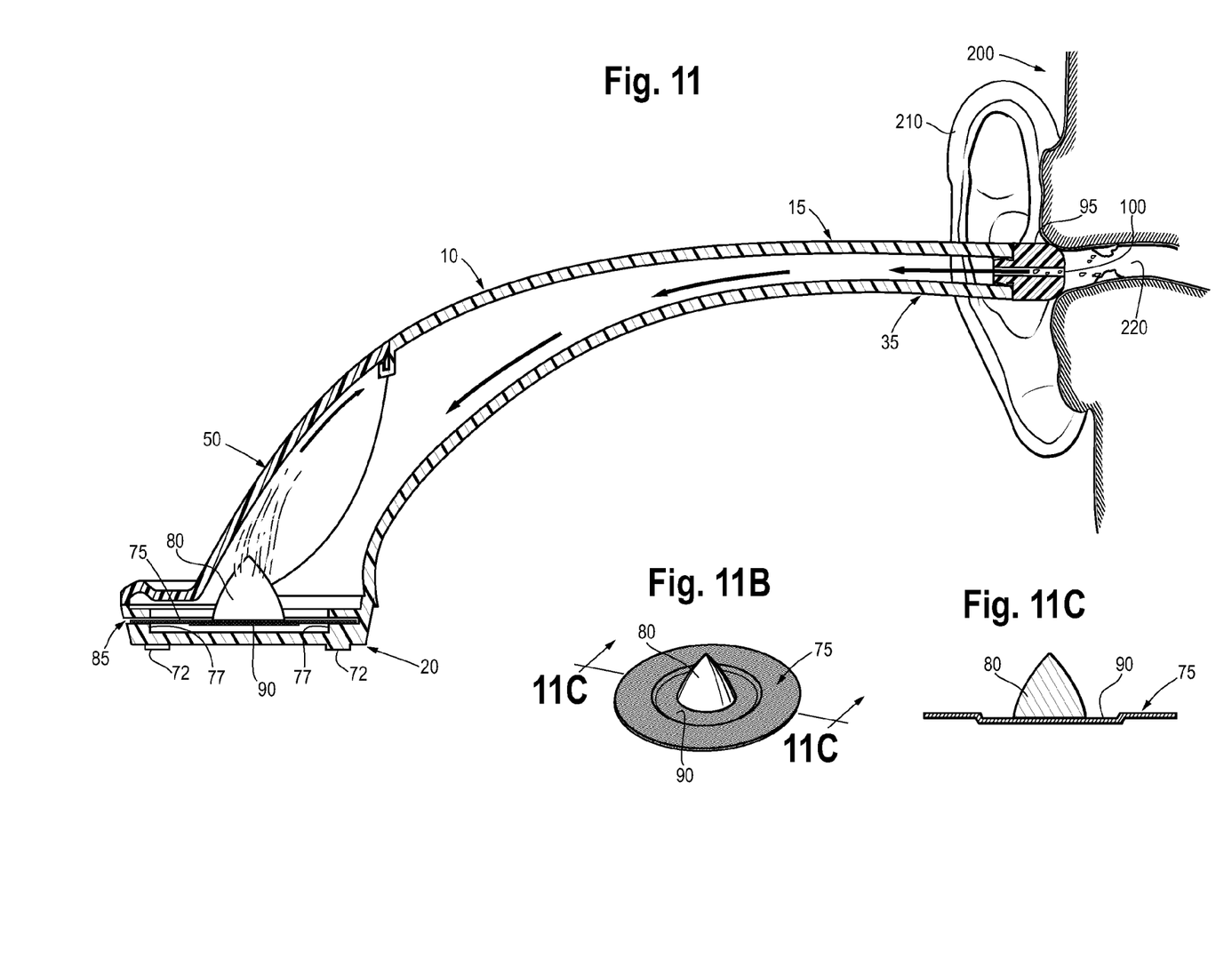
FIG. 11 shows a cross-sectional side view of an embodiment of the presently claimed invention as it appears when the presently claimed invention is in use.
FIGS. 11B and 11C show a perspective and cross-sectional views of an embodiment of a support member having an indentation.
Figure 12:
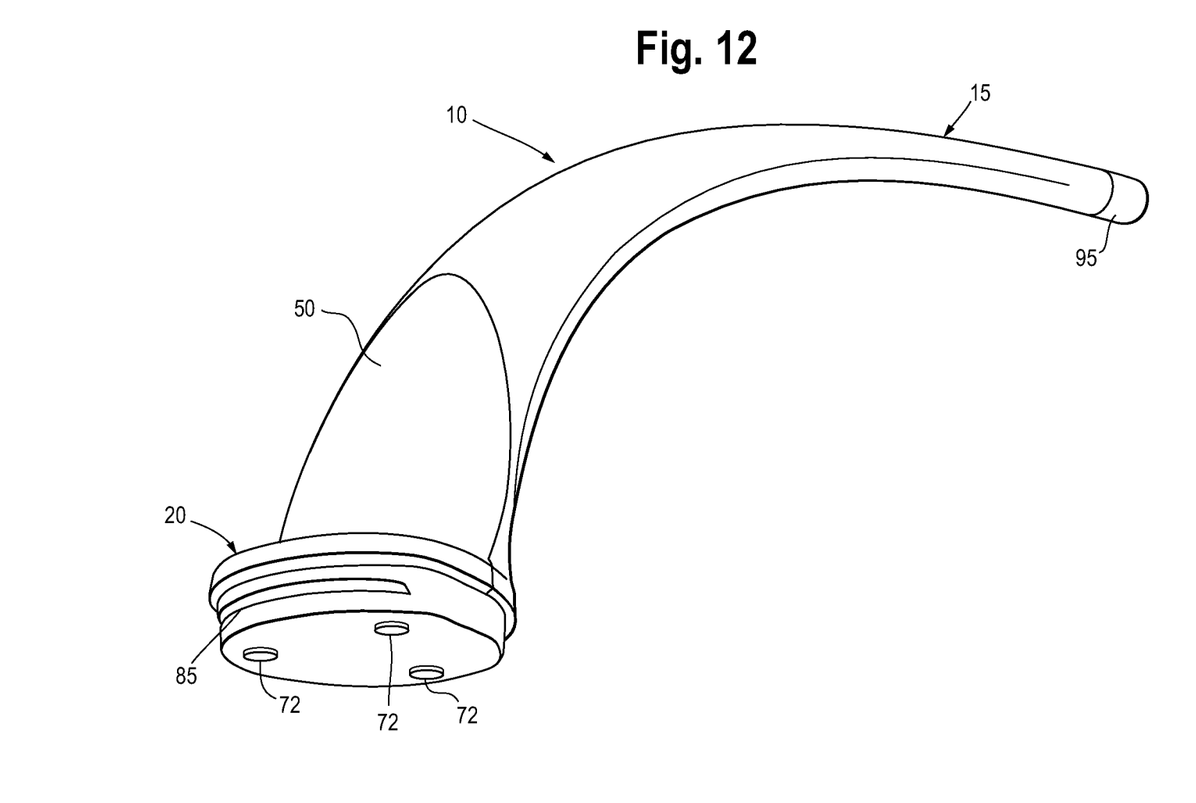
FIG. 12 shows a lower perspective view of an embodiment of the presently claimed invention showing support legs on the bottom of the bowl.

Referring to FIG. 7, the generally hollow body 15 comprises a bowl 20 that is made to receive ear pipe fuel 80. In one embodiment, the bowl is an integral part of the generally hollow body 15. In another embodiment, bowl 20 may comprise any generally concave shape. In another embodiment, the bowl 20 can be fixed or attached to the generally hollow body 15. In such embodiment, a variety of means may be used to attach the bowl 20 to the generally hollow body 15, including thread(s), bolt and nut, split pin(s), buckle(s), clamp(s), clasp(s), clip(s), nut(s) and bolt(s), screw(s), clutch(es), flange(s), band(s) of elastic or non elastic material, strap(s), hook-and-loop strip(s), magnet(s), and a combination thereof. Preferably, the lower portion of the bowl 20 has a substantially flat shape which may allow the pipe 10 to be placed on a flat surface (e.g., table, desk, or counter) without tipping and/or falling over. Since it may be desirable for the ear pipe 10, or some substantial portion thereof, to stand or sit on a flat surface, the various parts of the ear pipe, as described herein, will be made of appropriate materials having a weight, thickness, and/or density such that it will remain upright when placed on a flat surface. In addition, the bowl portion 20 of the generally hollow body 15 may optionally include short support legs, feet, or other small flattened protrusions on which the substantially flat bowl 20 may rest when in contact with a flat surface. In an embodiment, support legs(s) 72 are shown in FIGS. 3, 11, and 12.

The bowl 20 further comprises a support member 75 for supporting ear pipe fuel. Said support member may be an integral part of the generally hollow body 15, it may be an integral part of the bowl 20, or it may be a separate removable component. In one embodiment, the support member 75 comprises a wire mesh which can support a burning and/or smoldering quantity of ear pipe fuel 80. In another embodiment, the support member 75 has a diameter ranging from about 30 mm to about 90 mm. If the support member 75 is removable, it may be placed into the ear pipe 10 through an elongated outward-facing opening 85 that is located in the bowl 20 at its distal end and is substantially perpendicular to the vertical axis. In an embodiment, the angle of the elongated outward-facing opening 85 to the vertical axis ranges from about 85 degrees to about 95 degrees. Referring to FIG. 11, support member 75 can rest on a support ledge 77 in order to remain in place. The support ledge 77 can be generally circular or semi-circular within the bowl 20. The length of the elongated outward-facing opening 85 is approximately equal to the diameter or width of the of the support member 75 allowing the support member to securely slide into the bowl 20 of the ear pipe. For example, the width of the elongated outward-facing opening 85 may range from about 30 mm to about 90 mm. Furthermore, the elongated outward-facing opening 85 may serve as a means for ventilation required for the ear pipe fuel to properly burn and/or smolder. However, additional and/or separate ventilation opening(s) may be provided in or adjacent to the bowl 20 to change the characteristics of the air flow through the ear pipe.

In other embodiments, the support member 75 may be placed inside the ear pipe 10 through an opening left by the fuel cover 50 when said cover is removed, or in case of the pipe being separable along the transverse plane (as described above), directly from the top when the top portion is removed.

In yet another embodiment, the support member 75 may be a non-mesh, solid surface capable of supporting the burning and/or smoldering fuel. However, using a wire mesh as the support member 75 provides the advantage of supplying sufficient air flow to all parts of the ear pipe fuel so as to allow for a uniform burn and or smolder.

Referring to FIGS. 11, 11B, and 11C, preferably the support member 75 has a non-flat surface with an indentation(s) 90 towards the center. Such indentation allows the fuel to stay in the center of the support member 75 during pipe's movement, promoting a uniform and efficient burn and/or smolder.

Figure 8:
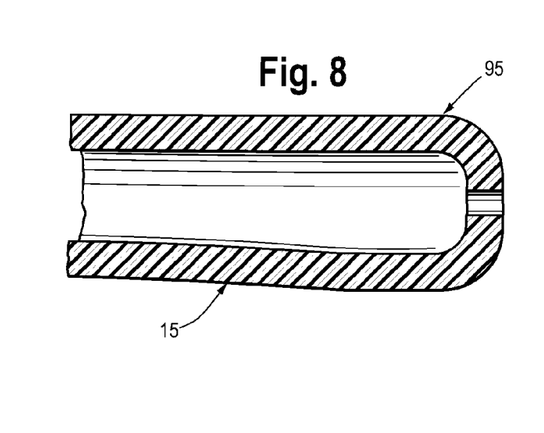
FIG. 8 shows a cross-sectional view of an embodiment where the ear tip is integrated into the generally hollow body.
Figure 9:
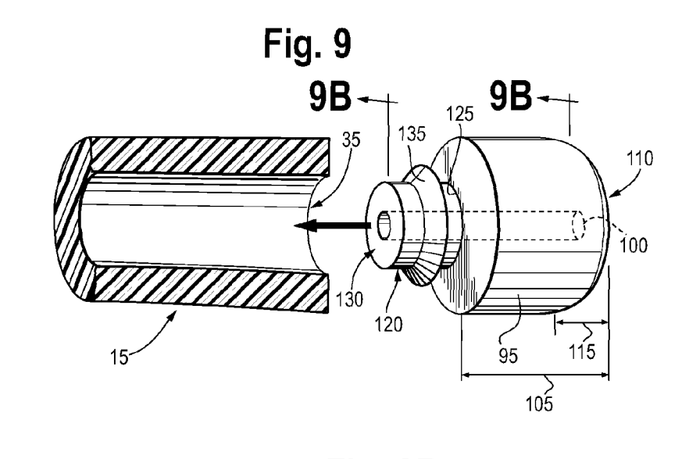
FIGS. 9, 9B, and 10 show cross-sectional views of embodiments where the ear tip is removable and capable of attachment/detachment to/from the generally hollow body.
Figure 10:
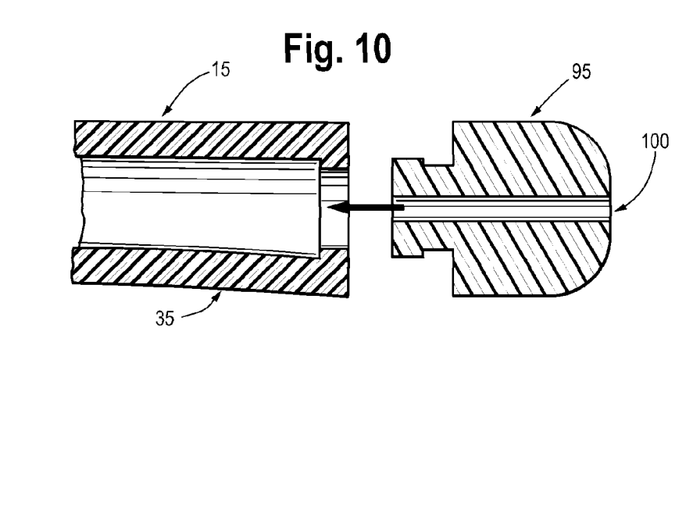

The ear pipe 10 further comprises an ear tip 95 disposed of at the proximal end 35 of the generally hollow body 15. The ear tip 95 may be an integral part of the generally hollow body 15 as seen in FIG. 8, or it may be a separate component capable of removal or exchange as shown in FIGS. 9 and 10. The ear tip 95 comprises an axially aligned pass-through opening 100 which allows for a flow of air and/or smoke from the smoldering ear pipe fuel 80 to pass from the generally hollow body 15 into the user's ear. The ear tip 95 further allows any and all debris drawn from the user's ear 210 to pass from the ear canal 220 back into the ear pipe for removal at a later time upon cleaning as illustrated in FIG. 11. In one embodiment, the inner diameter of the axially aligned pass-through opening 100 ranges from about 1 mm to about 6 mm.

Figure 9B:
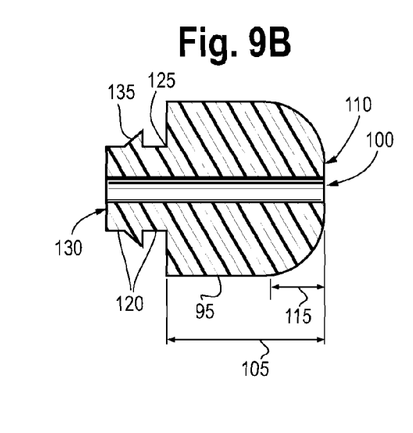

Now turning to FIGS. 9 and 9B, the ear tip 95 further comprises an ear contact portion 105 and an ear contact end 110. In one embodiment, the ear contact portion 105 is cone-shaped having a substantially flat outer surface that is tapered towards the axially aligned opening 100. In another embodiment, the ear contact portion 105 comprises a transitional region 115 which provides a smooth transition from the ear contact portion 105 to the ear contact end 110, thereby forming a smooth, outwardly convex annular rim. The smooth edge may allow the user to press the ear pipe against the ear canal creating a seal without much discomfort and/or pain. In yet another embodiment, the outer diameter of the ear contact portion ranges from about 8 mm to about 15 mm.

The ear tip 95 may further comprise a stem 120 distal to the ear contact end 110, wherein the stem can include a base 125 and an end 130. The stem 120 is intended to sealably connect the tip 95 to the open proximal end 35 in an embodiment where the tip is not an integral component of the generally hollow body 15. In one embodiment, the stem 120 has a substantially cylindrical shape with its outer diameter equal to or less than the inner diameter of the open proximal end 35 of the generally hollow body 15. In another embodiment, the outer diameter of the stem 120 ranges from about 2 mm to about 8 mm. Preferably, the outer diameter of the stem 120 is less than the inner diameter of the proximal end 35 of the generally hollow body 15, with the stem 120 comprising one or more elastomeric flange(s) or skirt(s) 135 angled towards the ear contact portion 105. Said elastomeric flange(s) 135 encircles the stem 120 and may be integral therewith. Having said flange(s) 135 angled towards the ear contact portion 105 allows the user to sealably attach the ear tip 95 to the generally hollow body 15 with relative ease while at the same time preventing unintentional displacement of said tip as some amount of force would be required to displace it.

FIG. 10 illustrates an embodiment of the presently claimed invention wherein an elastomeric protrusion(s) and/or a bump(s) may replace the flange(s) 135 to accomplish the same goal of preventing unintentional displacement of the ear tip 95 from the generally hollow body 15.

In yet another embodiment, the stem 120 is tapered from the stem base 125 towards the stem end 130. In this embodiment, the outer diameter at the stem base 125 is greater than the inner diameter of the proximal end 35 of the generally hollow body 15. The outer diameter of the stem 120 decreases towards the stem end 130, wherein the outer diameter at the stem end 130 is less than the inner diameter of the proximal end 35 of the generally hollow body 15. This embodiment may prevent the ear tip 95 from unintentional displacement from the generally hollow body 15 by having the outer surface of the stem 120 exert frictional force on the internal surface of the proximal end 35 of the generally hollow body 15.

Whereas the above-described embodiments describe the ear tip 95 fitting into the generally hollow body 15, other embodiments may include the generally hollow body 15 fitting into the ear tip 95. This may be accomplished by having the outer diameter of the proximal end 35 of the generally hollow body 15 be equal to or less than the internal diameter of the axially aligned opening 100.

In yet other embodiments, the ear tip 95 and the generally hollow body 15 may be joined together using any conventional means, including but not limited to using thread(s).

The tip may be made of any commercially available material that can be inserted into a human ear. In an embodiment, the material from which the tip is made is selected from wood, plastic, polycarbonate, metal, stone, clay, glass, ceramic, rubber, and any combination thereof. Preferably the ear tip 95 is disposable. In another embodiment, the ear tip 95 is made from hypoallergenic material.

Figure 13:
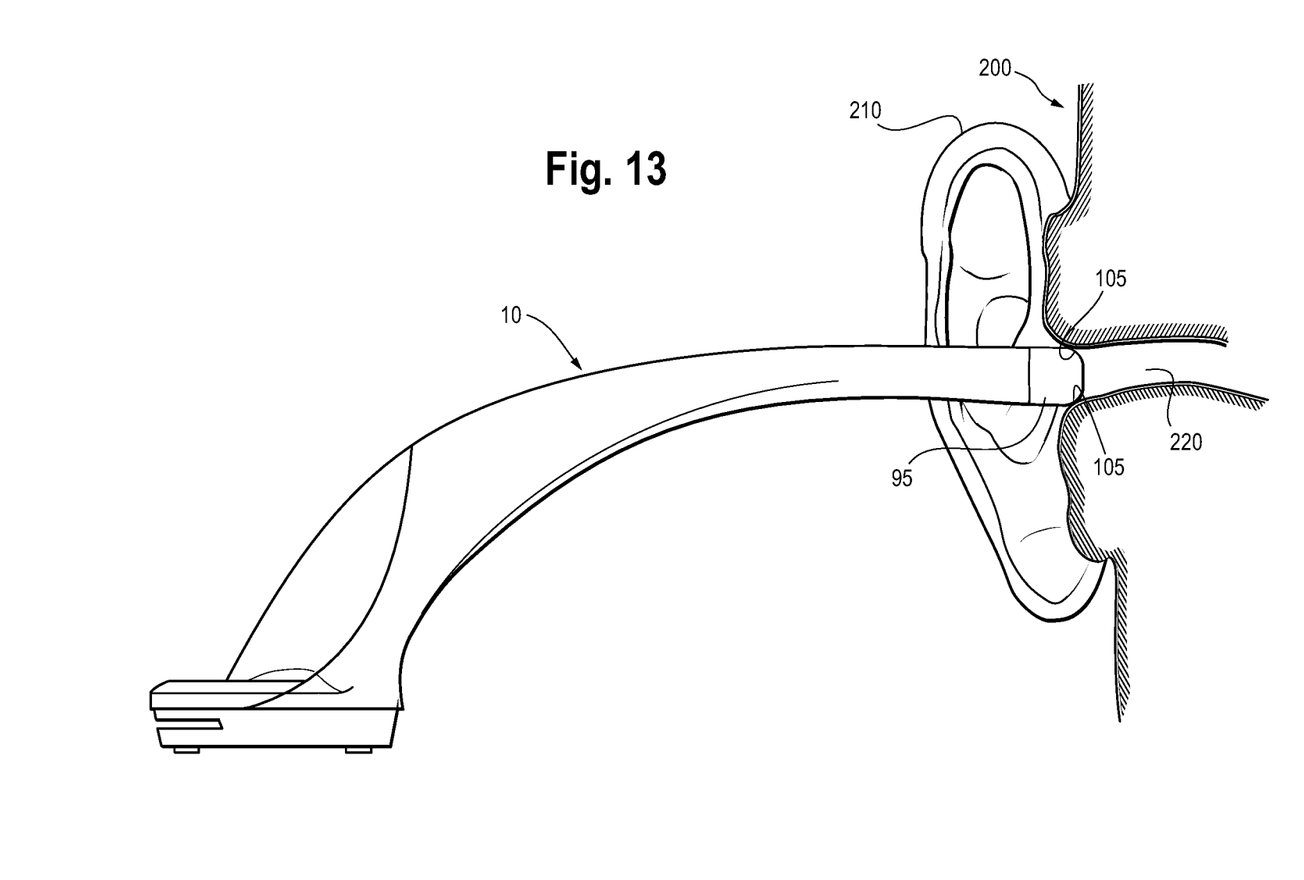
FIG. 13 shows a side view of an embodiment of the presently claimed invention in use.

The above-described and presently claimed invention may be used in various embodiments. For example, FIG. 13 illustrates the use of the ear pipe 10 by a user 200 and the correct orientation of the ear pipe 10 when inserted into the ear 210 of the user 200. Once the ear pipe fuel has been lit and has reached a smoldering state, and the fuel cover has been placed into a closed position, the proximal end 35 with the ear tip 95 of the ear pipe 10 is generally inserted into the ear canal 220 or in close proximity to the ear canal 220. Once the séance has been completed, the fuel cover may be removed and ear pipe fuel discarded. Depending on the embodiment, the ear pipe 10 may further be taken apart for cleaning any debris that may have collected on the internal surfaces thereof.

The ear pipe 10 may further be a part of a kit that comprises a generally hollow body, a fuel cover, one or more wire mesh fuel support members, one or more unit(s) of ear pipe fuel, and one or more ear tip(s). Optionally the ear tips may be of varying size and/or material to allow for better fitting and improved comfort depending on the user. In another embodiment, the kit may further comprise a cleaning device and/or solution that may aid in cleaning and/or removing the debris collected and/or left over inside the ear pipe after the use thereof.

In one embodiment, the above-described and presently claimed invention may be used comprising the following steps:
 a. removing the fuel cover 50 from the pipe 10;
 b. placing the support member 75 inside the ear pipe;
 c. placing the ear pipe fuel 80 on top of fuel support member 75;
 d. providing an ignition source to ignite the ear pipe fuel;
 e. allowing the fuel to remain lit for a period of time that is sufficient to permit the fuel to begin and sustain a smoldering process;
 f. extinguish the flame on the fuel by blowing it out or by replacing the fuel cover 50 into its intended position, thereby causing the fuel to smolder and produce smoke and/or warm air that will travel in the upward direction along the generally hollow body 15 and exit from the proximal end 35 and the ear tip 95;

g. while keeping the pipe substantially level, pressing the ear tip 95 to the ear canal 220 to allow the smoke and/or warm air to enter the canal 220; and h. continuing step (g) for a period of time that is sufficient to realize the benefits of using the device such as drawing ear wax, pathogens, and other debris from the ear 210 outward through and away from the canal 220 into and through the generally hollow body 15 of the ear pipe 10.

It must be remembered, that the various embodiments described above may include, in addition to the parts of the presently claimed invention, addition shapes, forms, materials, finishes, and fuels suitable for use in these embodiments. Furthermore, these embodiments are non-limiting, and therefore variations of these embodiments will become apparent to those of ordinary skill in the art upon reading the description. Accordingly, this invention includes all modifications and equivalents of the subject matter recited in the claims appended hereto as permitted by applicable law.

All references, including publications, patent applications, and patents, cited herein are hereby incorporated by reference to the same extent as if each reference was individually and specifically indicated to be incorporated by reference and was set forth in its entirety herein.

The use of the terms "a," "an," "the," and similar referents in the context of describing the presently claimed invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the terms "about" and "approximately" are the equivalent of a stated value+/−10%. Thus a value of about 5 centimeters (cm) refers to the range of values from and including 4.5 cm to and including 5.5 cm.

While some potential advantages and objects are being expressly identified herein, it should be understood that some embodiments of the invention may not provide all, or any, of the expressly identified advantages and objects.

What is claimed:

1. A pipe for delivery of warm air and/or smoke to an ear of a user, the pipe comprising a generally hollow body, wherein the generally hollow body includes:
   at least one unit of ear pipe fuel;
   a bowl disposed at a distal end of the pipe, said bowl further comprising a support member positioned within or adjacent to the bowl which supports the at least one unit of ear pipe fuel;
   a midsection; and
   a proximal end having an ear tip;
   wherein the midsection extends upward from at least a portion of an upper surface of the bowl to the proximal end of the generally hollow body, wherein the proximal end having an ear tip is open,
   said ear tip including an ear contact portion having a smooth, outwardly convex ear contact end adapted to be inserted comfortably into the ear canal of the user.

2. The pipe of claim 1, wherein the midsection is tapered towards the proximal end.

3. The pipe of claim 1, wherein at least a portion of the midsection comprises a flexible section, wherein the flexible section is adjustable between the proximal end and the distal end.

4. The pipe of claim 1, wherein the generally hollow body is made from a material selected from the group consisting of wood, plastic, polycarbonate, metal, stone, clay, glass, ceramic, rubber, and combinations thereof.

5. The pipe of claim 1, further comprising a fuel cover disposed adjacent to the upper surface of the bowl.

6. The pipe of claim 5, wherein the fuel cover arches over the upper surface of the bowl and covers the bowl.

7. The pipe of claim 6, wherein the fuel cover is made from a material selected from the group consisting of wood, plastic, polycarbonate, metal, stone, clay, glass, ceramic, rubber, and combinations thereof.

8. The pipe of claim 6, wherein the fuel cover comprises at least one ventilation opening.

9. The pipe of claim 1, wherein the bowl comprises an elongated outward-facing opening located at its distal end, wherein the elongated outward-facing opening is substantially perpendicular to a vertical axis.

10. The pipe of claim 1, wherein the support member comprises a wire mesh.

11. The pipe of claim 1, further comprising a support ledge within the bowl, and a support member placed on the support ledge.

12. The pipe of claim 1, wherein the generally hollow body comprises a first portion and a second portion, the first and second portions separable along a sagittal plane, wherein said separation divides the pipe into essentially equal parts.

13. The pipe of claim 1, wherein the generally hollow body comprises a top portion and a bottom portion, the top and bottom portions separable along a transverse plane.

14. A pipe for delivery of warm air and/or smoke to an ear of a user, the pipe comprising:
   a generally hollow body, wherein the generally hollow body includes
     at least one unit of ear pipe fuel;
     a bowl disposed at a distal end of the pipe, said bowl further comprising a support member positioned within or adjacent to the bowl which supports the at least one unit of ear pipe fuel,
     a midsection, and a proximal end, wherein the midsection extends upward from at least a portion of an upper surface of the bowl to the proximal end of the generally hollow body, wherein the proximal end is open; and
   an ear tip positioned adjacent to the proximal end of the generally hollow body, wherein the ear tip includes
     an axially aligned pass-through opening;
     an ear contact portion; and
     a smooth, outwardly convex ear contact end adapted to be inserted comfortably into the ear canal of the user.

15. The pipe of claim 14, wherein the ear contact portion is cone-shaped having a substantially flat outer surface that is tapered towards the ear contact end.

16. The pipe of claim 14, wherein the ear contact portion further comprises a transitional region that provides a smooth transition to the ear contact end forming a smooth, outwardly convex annular rim adapted to be inserted comfortably into the ear canal of the user.

17. The pipe of claim 14, wherein the ear tip is detachable from the generally hollow body.

18. The pipe of claim 14, wherein the ear tip further comprises a stem disposed distal to the ear contact end, the stem having a stem base and a stem end.

19. The pipe of claim 18, wherein the stem comprises at least one elastomeric flange that surrounds the stem.

20. The pipe of claim 18, wherein the stem is tapered from the stem base towards the stem end.

21. The pipe of claim 20, wherein the opening of the proximal end of the generally hollow body has a first internal diameter, the stem base has a second external diameter, the stem end has a third external diameter, and wherein the first internal diameter is less than or equal to the second external diameter and wherein the first internal diameter is greater than the third external diameter.

22. A kit comprising:
a) a pipe for delivery of warm air and/or smoke to an ear of a user, the pipe comprising a generally hollow body with an external and an internal surface, wherein the generally hollow body includes,
   a bowl disposed at a distal end of the pipe, a midsection extended upward from at least a portion of an upper surface of the bowl to a proximal end of the generally hollow body wherein the proximal end is open, a fuel cover arching over the upper surface of the bowl and covering the bowl, and at least one support member positioned within and supported by the bowl;
b) at least one ear tip, wherein the tip is positioned adjacent to the proximal end of the generally hollow body, said at least one ear tip including an ear contact portion having a smooth, outwardly convex ear contact end adapted to be inserted comfortably into the ear canal of the user; and
c) at least one unit of ear pipe fuel supported by the support member.

* * * * *